(12) United States Patent
Meldrum et al.

(10) Patent No.: US 10,391,485 B2
(45) Date of Patent: Aug. 27, 2019

(54) MICROFLUIDIC ELECTROCAGE DEVICE AND CELL MEDIUM FOR TRAPPING AND ROTATING CELLS FOR LIVE-CELL COMPUTED TOMOGRAPHY (CT)

(71) Applicant: Arizona Board of Regents, a body corporate of the State of Arizona, acting for and on behalf of Arizona State University, Scottsdale, AZ (US)

(72) Inventors: Deirdre Meldrum, Phoenix, AZ (US); Roger Johnson, Phoenix, AZ (US); Iniyan Soundappa Elango, Hillsboro, OR (US); Andrew Shabilla, Scottsdale, AZ (US); Hong Wang, Tempe, AZ (US); Jakrey Myers, Scottsdale, AZ (US); Laimonas Kelbauskas, Gilbert, AZ (US); Dean Smith, Phoenix, AZ (US); Pimwadee Limsirichai, Chandler, AZ (US)

(73) Assignee: ARIZONA BOARD OF REGENTS, A BODY CORPORATE OF THE STATE OF ARIZONA, ACTING FOR AND ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 421 days.

(21) Appl. No.: 14/497,005

(22) Filed: Sep. 25, 2014

(65) Prior Publication Data
US 2015/0087007 A1 Mar. 26, 2015

Related U.S. Application Data

(60) Provisional application No. 61/882,117, filed on Sep. 25, 2013.

(51) Int. Cl.
| | | |
|---|---|---|
| *B01L 3/00* | (2006.01) | |
| *C23F 1/30* | (2006.01) | |
| *C23F 1/02* | (2006.01) | |
| *C23F 1/44* | (2006.01) | |
| *C12M 3/06* | (2006.01) | |
| *C12M 1/34* | (2006.01) | |

(52) U.S. Cl.
CPC ....... *B01L 3/502707* (2013.01); *C12M 23/16* (2013.01); *C12M 41/36* (2013.01); *C23F 1/02* (2013.01); *C23F 1/30* (2013.01); *C23F 1/44* (2013.01); *B01L 3/502761* (2013.01); *B01L 2300/0645* (2013.01)

(58) Field of Classification Search
CPC .......... H01L 21/283; H01L 21/312; H01L 21/31056; B01L 2300/0645; B01L 3/502761

USPC .................................................. 430/318, 328
See application file for complete search history.

(56) References Cited

U.S. PATENT DOCUMENTS

| | | | |
|---|---|---|---|
| 2006/0279025 A1 | 12/2006 | Heidari et al. | |
| 2007/0031819 A1* | 2/2007 | Koschwanez | B01L 3/502707 435/4 |
| 2007/0217957 A1* | 9/2007 | Flachsbart | B01L 3/502707 137/803 |
| 2008/0166656 A1* | 7/2008 | Moon | G03F 7/0233 430/270.1 |
| 2009/0250130 A1* | 10/2009 | Studer | B81C 1/00119 137/833 |
| 2011/0100817 A1* | 5/2011 | Dorairaj | C07K 1/26 204/451 |
| 2013/0338267 A1 | 12/2013 | Appleby et al. | |

OTHER PUBLICATIONS

Saha et al., 2001. A Versatile and Inexpensive Apparatus for Rapid Parallel Synthesis on Solid Support: Description and Synthesis Illustration. Journal of Combinatorial Chemistry, vol. 3, pp. 181-188.*
Hui, Y.H. et al., "Handbook of Food Science, Technology, and Engineering, vol. 1," CRC Press, Dec. 2005, p. 4-2.
Lee, Seok Jae et al., "Multidirectional Tilted UV Lithography: A Key Fabrication Method of Polymeric Microflidic Device," 17th International Conference on Miniaturized Systems for Chemistry and Life Sciences, Oct. 27-31, 2013, Freiburg, Germany, pp. 1424-1426.
Yoon, Yong-Kyu et al., "Multidirectional UV Lithography for Complex 3-D MEMS Structures," Journal of Microelectromechanical Systems, vol. 15, No. 5, Oct. 2006, IEEE, pp. 1121-1130.
Zhang, Wenjie et al., "Simulation and Experimental Characterization of Microscopically Accessible Hydrodynamic Microvortices," Micromachines, vol. 3, Issue 2, Jun. 15, 2012, MDPI, pp. 529-541.

* cited by examiner

*Primary Examiner* — Daborah Chacko-Davis
(74) *Attorney, Agent, or Firm* — Withrow & Terranova, P.L.L.C.; Vincent K. Gustafson

(57) ABSTRACT

A microfluidic device useable for performing live cell computed tomography imaging is fabricated with a cover portion including a first wafer with at least one metal patterned thereon, a base portion including a second wafer with at least one metal patterned thereon and negative photoresist defining recesses therein, and a diffusive bonding layer including a negative photoresist arranged to join the cover portion and the base portion. A composition useful in live cell computer topography includes a long-chain polysaccharide at a concentration of from about 0.01% to about 10.0% in cell culture medium for supporting cell life while enabling cell rotation rate to be slowed to a speed commensurate with low light level imaging.

11 Claims, 4 Drawing Sheets

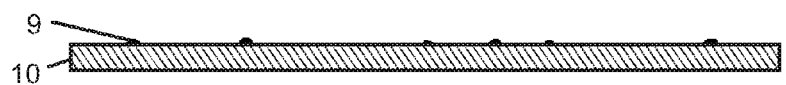
FIG._1A
FIG._1B
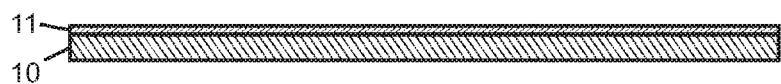
FIG._1C
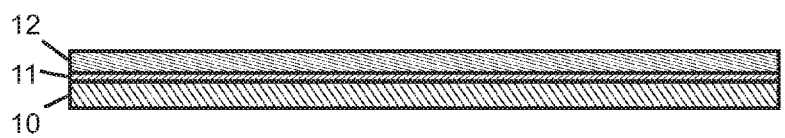
FIG._1D
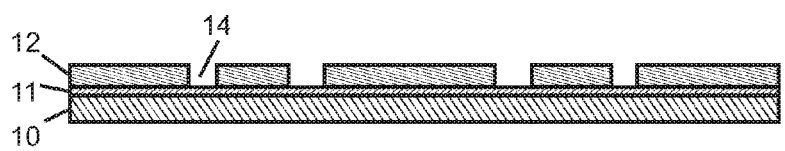
FIG._1E
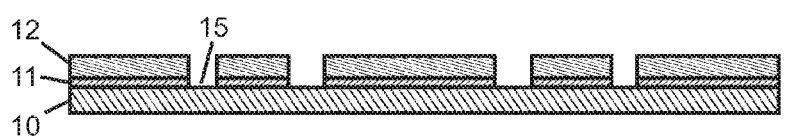
FIG._1F
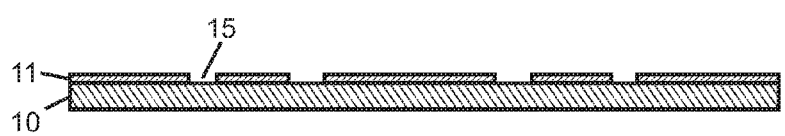
FIG._1G
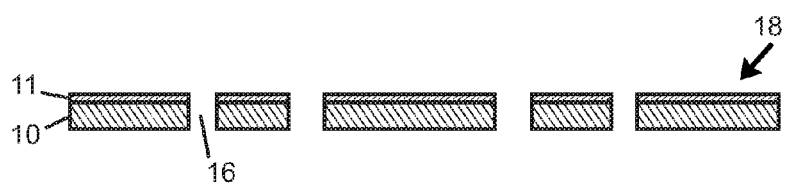
FIG._1H

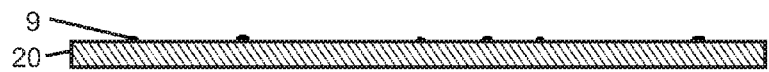
FIG._2A
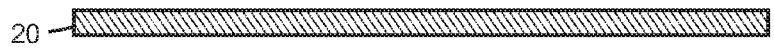
FIG._2B
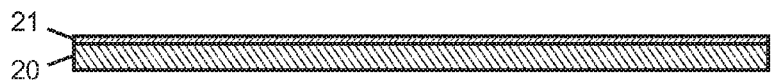
FIG._2C
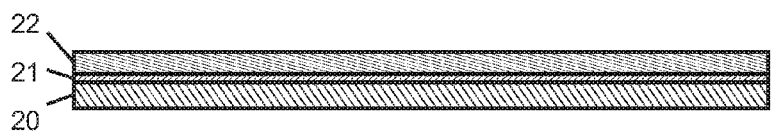
FIG._2D
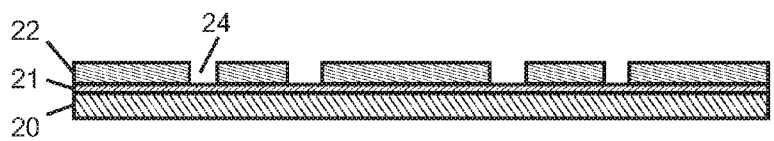
FIG._2E
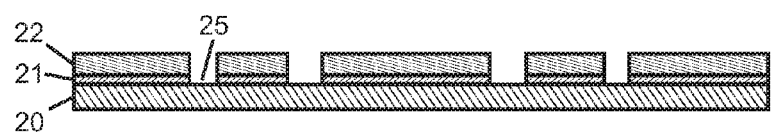
FIG._2F
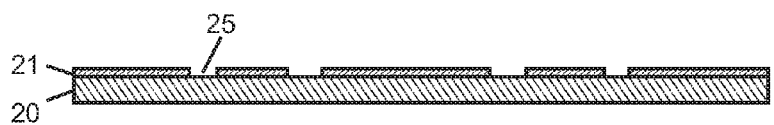
FIG._2G
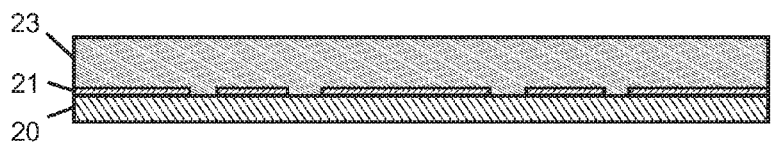
FIG._2H
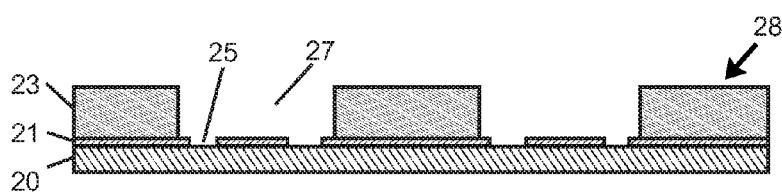
FIG._2I

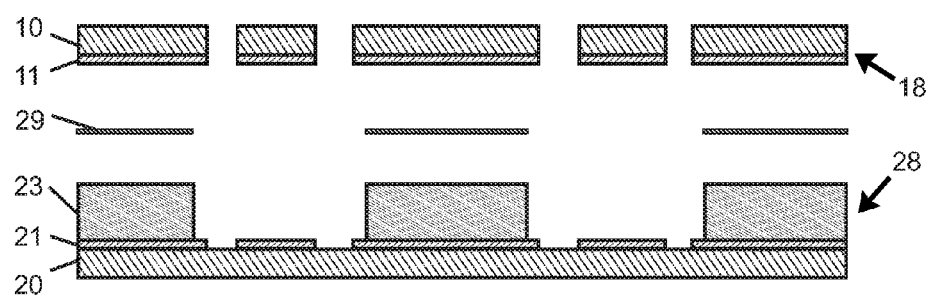
FIG._3A
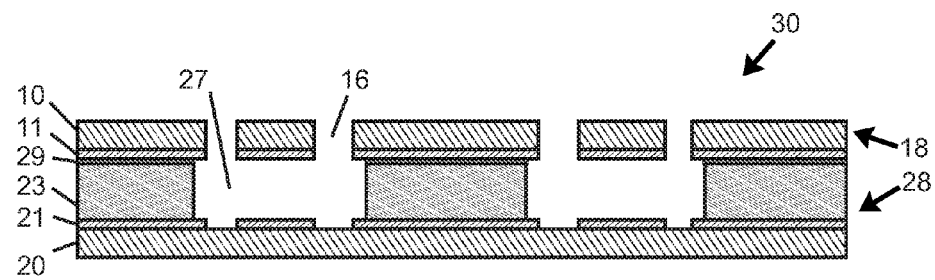
FIG._3B

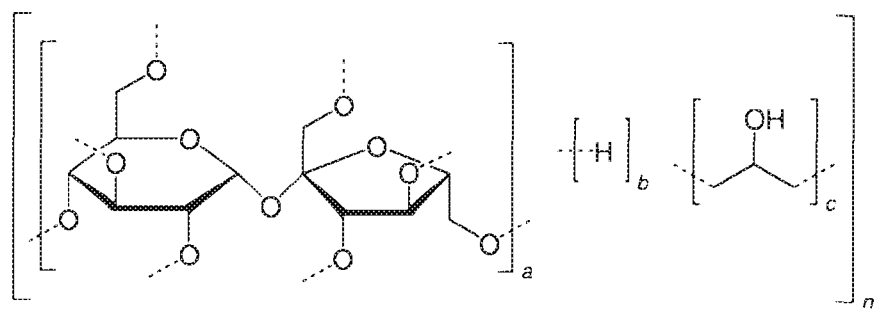
FIG._4A
(RELATED ART)
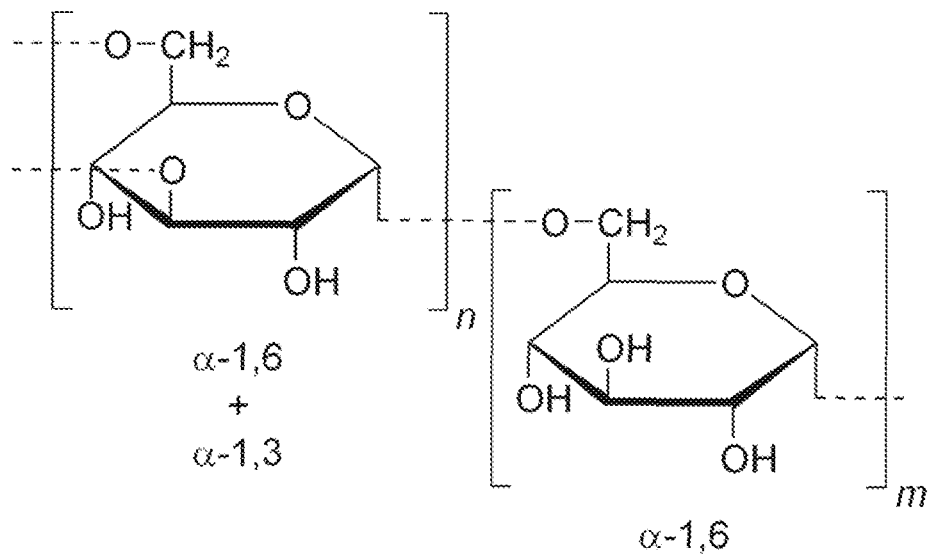
FIG._4B
(RELATED ART)

MICROFLUIDIC ELECTROCAGE DEVICE AND CELL MEDIUM FOR TRAPPING AND ROTATING CELLS FOR LIVE-CELL COMPUTED TOMOGRAPHY (CT)

STATEMENT OF RELATED APPLICATION(S)

This application claims benefit of U.S. Provisional Patent Application No. 61/882,117 filed on Sep. 25, 2013. The contents of the foregoing application are hereby incorporated by reference as if fully set forth herein.

TECHNICAL FIELD

Aspects of this disclosure relate to fabrication, sealing by diffusive bonding layer, and use of microfluidic devices, such as may include glass or silicon materials. Aspects of this disclosure further relate to a high viscosity medium useful for suspending cells for imaging, and production and use of such a medium.

BACKGROUND

Computed tomography (CT) imaging of freely suspended particles, including live single cells and cell clusters, is made possible by recent developments in low-light level imaging and other detectors, microelectronics, microfluidics, and high-speed computing. To perform three-dimensional (3D) imaging, it is necessary to have the ability to hold microscopic particles precisely in free suspension and to slowly rotate them. One way particles can be manipulated is via the influence of electric fields in field cages (also known as electrocages). An array of microelectrodes rotates particles by application of dielectrophoretic forces. These electrodes are typically fabricated by semiconductor technology methods. This fabrication is on a micro scale and can be very tricky to accomplish. Aspects of this disclosure propose a fabrication method aimed at addressing shortcomings of conventional methods.

It has proven very difficult to rotate the particles at a rate slow enough to allow low light-level data acquisition. This invention also provides a method for producing and using a cell medium suitable for supporting cell life and cell function, while enabling rotation rate to be slowed to a speed commensurate with low light-level imaging.

SUMMARY

The diffusive bonding layer method set forth in this application permits simpler design, fabrication, and bonding procedures as compared to traditional high pressure/temperature bonding. Due to the high strength and consistency of the diffusive bonding layer, there is a greater freedom in design of channels and other microfeatures. This is due to the absence of large voids in the bonded area, which are often formed in the use of other techniques. Designs can also be of much higher tolerance, as alignment for the diffusive bonding layer technique is inherently more precise. Fabrication is made easier by allowing for a single layer of photoresist to be used for two wafers or chips, rather than one layer per substrate. Bonding itself is also cheaper, as a wafer bonder is not required to carry out the process. While the complexity of the bonding itself may be slightly higher when compared to high pressure/temperature techniques, the diffusive bonding layer technique is more robust. The diffusive bonding layer conforms to the intrinsic surface abnormalities of the substrates to be bonded. It also does not require extensive tuning or precise process control, as a high pressure/temperature bonding process does. The diffusive bonding layer technique can also be applied to temperature sensitive materials, and delicate microfeatures, which cannot withstand high temperatures or pressures.

In certain aspects, the disclosure relates to a method of fabricating a microfluidic device useable to perform live cell computed tomography imaging, the method comprising: cleaning (e.g., RCA cleaning) a first wafer and a second wafer; depositing at least one metal layer on each of the first wafer and the second wafer; depositing a positive photoresist layer over the deposited at least one metal layer of each of the first wafer and the second wafer; impinging UV light on portions of the positive photoresist layer of each of the first wafer and the second wafer to pattern the positive photoresist layer and expose regions of the at least one metal layer on each of the first wafer and the second wafer; wet etching the exposed regions of the at least one metal layer on each of the first wafer and the second wafer to pattern the at least one metal layer; removing the positive photoresist layer of each of the first wafer and the second wafer; defining at least one aperture through the first wafer, whereby after such at least one aperture is defined, a microfluidic device cover portion is obtained; coating the second wafer with first negative photoresist to cover the patterned at least one metal layer; impinging UV light on portions of the first negative photoresist coating the second wafer to pattern the first negative photoresist layer, thereby defining recesses in the first negative photoresist layer and exposing regions of the at least one metal layer on the second wafer, to form a microfluidic device base portion; and bonding the microfluidic device cover portion and the microfluidic device base portion using a UV curable bonding agent (e.g., a second negative photoresist or a UV adhesive). In certain aspects, the at least one metal layer may comprise a chromium layer and a gold layer overlying the chromium layer.

This disclosure also provides a high viscosity cell medium that provides a means to simultaneously support cell life in the electrocage and slow the cell/cell cluster rotation rate. Such a medium allows for a lower angular velocity, and higher lateral stability rotation of cells, cell clusters, or particles when compared to regular aqueous growth medium. The slower rotation allows for longer detector (camera) integration times as well as efficient use of frame rate, both of which improve reconstruction quality. The improved lateral stability allows for decreased distortion and blur degradation in the reconstruction. It also allows for faster reconstruction, as less processing power would be necessary to discriminate the angular and translational position of the rotating object.

In certain aspects, the disclosure relates to a method of adjusting viscosity of an aqueous solution used in live cell computed tomography, the method comprising adding a long-chain polysaccharide to an aqueous solution. The aqueous solution preferably comprises a cell culture medium. The long-chain polysaccharide may comprise at least one of Ficoll® and dextran polysaccharides.

In certain aspects, the disclosure relates to a composition useful in live cell computer topography, the composition comprising a long-chain polysaccharide at a concentration of from about 0.01% to about 10.0% in cell culture medium.

In further aspects, one or more of the foregoing aspects or any other features disclosed herein may be combined for additional advantage.

BRIEF DESCRIPTION OF THE DRAWINGS

In the drawings, features are not drawn to scale unless expressly indicated to the contrary herein.

FIG. 1A is a side cross-sectional view of a first wafer useful for fabricating a cover portion of a microfluidic device according to the present disclosure, prior to cleaning of the first wafer.

FIG. 1B is a side cross-sectional view of the first wafer of FIG. 1A following cleaning (e.g., RCA cleaning).

FIG. 1C is a side cross-sectional view of the first wafer of FIG. 1B following deposition of at least one metal layer (e.g., a chromium adhesion layer and a gold layer).

FIG. 1D is a side cross-sectional view of the first wafer and at least one metal layer of FIG. 1C following deposition of a positive photoresist mask layer over the at least one metal layer.

FIG. 1E is a side cross-sectional view of the first wafer and layers of FIG. 1D, following exposure and patterning of the photoresist mask layer to expose regions of the at least one metal layer.

FIG. 1F is a side cross-sectional view of the first wafer and layers of FIG. 1E, following etching to remove exposed regions of the at least one metal layer and thereby pattern the at least one metal layer.

FIG. 1G is a side cross-sectional view of the first wafer and patterned at least one metal layer of FIG. 1F, following microstripper cleaning to remove the positive photoresist mask layer.

FIG. 1H is a side cross-sectional view of the first wafer and patterned at least one metal layer of FIG. 1G, following laser milling of holes through the first wafer, thereby yielding a cover portion of a microfluidic (e.g., electrocage) device.

FIG. 2A is a side cross-sectional view of a second wafer useful for fabricating a base portion of a microfluidic device according to the present disclosure, prior to cleaning of the second wafer.

FIG. 2B is a side cross-sectional view of the second wafer of FIG. 2A following cleaning (e.g., RCA cleaning).

FIG. 2C is a side cross-sectional view of the second wafer of FIG. 2B following deposition of at least one metal layer (e.g., a chromium adhesion layer and a gold layer).

FIG. 2D is a side cross-sectional view of the second wafer and at least one metal layer of FIG. 2C following deposition of a positive photoresist mask layer over the at least one metal layer.

FIG. 2E is a side cross-sectional view of the second wafer and layers of FIG. 2D, following exposure and patterning of the photoresist mask layer to expose regions of the at least one metal layer.

FIG. 2F is a side cross-sectional view of the second wafer and layers of FIG. 2E, following etching to remove exposed regions of the at least one metal layer and thereby pattern the at least one metal layer.

FIG. 2G is a side cross-sectional view of the second wafer and patterned at least one metal layer of FIG. 2F, following microstripper cleaning to remove the positive photoresist mask layer.

FIG. 2H is a side cross-sectional view of the second wafer and patterned at least one metal layer of FIG. 2G following coating with a negative photoresist.

FIG. 2I is a side cross-sectional view of the second wafer, at least one metal layer, and negative photoresist layer of FIG. 2H, following exposure and patterning of the negative photoresist layer to define cavities therein and expose regions of the at least one metal layer, thereby yielding a base portion of a microfluidic (e.g., electrocage) device.

FIG. 3A is an exploded side cross-sectional view of portions of a microfluidic device prior to assembly thereof, including the cover portion of FIG. 1H aligned with the base portion of FIG. 2I, with a negative photoresist (diffusive bonding) material layer arranged between the cover portion and the base portion.

FIG. 3B is a side cross-sectional view of an assembled microfluidic device including the cover portion of FIG. 1H, the base portion of FIG. 2I, and the negative photoresist layer joining the cover portion and the base portion.

FIG. 4A is a chemical diagram depicting the structure of a Ficoll® polysaccharide.

FIG. 4B is a chemical diagram depicting the structure of a dextran polysaccharide.

DETAILED DESCRIPTION

In certain aspects, the disclosure relates to a method of fabricating a microfluidic device useable to perform live cell computed tomography imaging. Various steps of a method will be described in connection with FIGS. 1A-1H (which depict fabrication of a cover portion of a microfluidic device utilizing a first wafer), in connection with FIGS. 2A-2I (which depict fabrication of a base portion of a microfluidic device utilizing a second wafer), and in connection with FIGS. 3A-3B (which depict joining of the base portion and the cover portion of the microfluidic device with an intermediate diffusive bonding layer).

Certain method steps disclosed herein utilize positive or negative photoresists. Photoresists are available in both positive tone and negative tone variants. A positive tone resist (also called a positive photoresist) is exposed with UV light where the underlying material is to be removed. Exposure to the UV light changes the chemical structure of a positive tone resist so that it becomes more soluble in the developer. The exposed resist is then washed away by the developer solution, leaving windows of the bare underlying material. The mask, therefore, contains an exact copy of the pattern which is to remain on the wafer, as a stencil for subsequent processing. Negative tone resists behave in the opposite manner. When exposed to the UV light, a negative tone photoresist (also called a negative photoresist) becomes crosslinked/polymerized, and more difficult to dissolve in developer. Therefore, the negative photoresist remains on the surface of the substrate where it is exposed, and the developer solution removes only the unexposed areas. Masks used for negative photoresists, therefore, contain the inverse or photographic "negative" of the pattern to be transferred.

Various negative photoresists are commercially available from Microchem Corp. (Newton, Mass., USA) (a subsidiary of Nippon Kayaku Co. Ltd. of Tokyo, Japan), including SU-8 family and the KMPR® (a registered trademark of Microchem Corp.) negative photoresist product lines. SU-8 resists were first commercially introduced by MicroChem in 1996 and formulated in gamma butyrolactone (GBL) solvent. MicroChem subsequently introduced the SU-8 2000 series (which are formulated in cyclopentanone solvent) and the SU-8 3000 series (an improved formulation of SU-8 2000). SU-8, SU-8 2000, and SU-8 3000 (all SU-8 family) resists are optically transparent, solvent developable, highly functional epoxies. KMPR® 1000 series i-line photoresist is a high contrast, epoxy based photoresist that can be developed in a conventional aqueous alkaline developer (2.38% TMAH (0.26N)) and readily stripped from a wafer. KMPR® 1000 series resists are available in four standard viscosities (95 cSt corresponding to KMPR® 1005; 600 cSt corresponding to KMPR® 1010; 4800 cSt corresponding to KMPR® 1025; and 13,000 cSt corresponding to KMPR® 1050). One difference between KMPR® and SU-8 negative photoresists is that KMPR® negative photoresists can be readily removed using commercially available chemical removers.

A method of fabricating a microfluidic device may utilize first and second wafers (e.g., silicon, silicon dioxide, silicon nitride, silicon carbide, glass (including borosilicate glass), or other suitable material). An initial step may involve cleaning the wafers, preferably according to a RCA cleaning process such as known in the art (e.g., removing the organic contaminants using a solution of 5 parts deionized water, 1 part aqueous $NH_4OH$, and 1 part aqueous $H_2O_2$; followed by an optional oxide layer removal step including short immersion in a 1:100 or 1:50 solution of $HF+H_2O$ at 75 or 80° C.[1] typically for 10 minutes; followed by removal of ionic contaminants using a solution of 5 parts deionized water, 1 part aqueous HCl, and 1 part aqueous $H_2O_2$); and followed by suitable rinsing and drying. A first wafer 10 including contaminants 9 thereon is shown FIG. 1A, and a second wafer 20 including contaminants 9 thereon is shown in FIG. 2A. Following performance of a suitable (e.g., RCA) cleaning procedure, the first wafer 10 is preferably substantially free of contaminants such as shown in FIG. 1B, and the second wafer 20 is preferably substantially free of contaminants such as shown in FIG. 2B.

Following cleaning, at least one metal layer is deposited on each of the first wafer and the second wafer. Such metal layer should preferably be of sufficient conductivity to function as one or more electrodes. Any suitable metal may be used such as (but not limited to) gold, nickel, copper, indium, platinum, aluminum, alloys based on one or more of the foregoing metals, and the like. Preferably an adhesion layer such as chromium is deposited first on the wafer, and then a more conductive metal such as gold is deposited thereafter. Gold is particularly preferred for its electrical properties and its superior resistance to corrosion and oxidation. In certain embodiments, a chromium layer having a thickness of about 20 nm is deposited first, followed by a gold layer having an increased thickness of about 200 nm. Metal layers of other thicknesses may be used. In certain embodiments, transparent conductive oxides may be substituted for one or more metal layers, with non-limiting examples of transparent conductive oxides including indium tin oxide (ITO), gallium indium tin oxide (GITO), and zinc indium tin oxide (ZITO). FIG. 1C shows a first wafer 10 having at least one metal layer 11 (which may include multiple metal sublayers) thereon, and FIG. 2C shows a second wafer 20 having at least one metal layer 21 (which may include multiple metal sublayers) thereon.

After deposition of the at least one metal layer, a positive photoresist layer is applied over the metal layer(s) of each of the first wafer and the second wafer. The positive photoresist layer serves as a mask. In certain embodiments, the positive photoresist layer may have a thickness on the order of about 1 micron. An example of a suitable positive photoresist is an AZ® 3312 photoresist, as a member of the AZ® 3300 series photoresist (formulated using a mixture of propylene glycol monomethyl ether acetate (PGMEA) and ethyl lactate solvents) commercially available from Arizona Electronic Materials (Somerville, N.J., USA). AZ® is a registered trademark of Arizona Electronic Materials. Other photoresists may be used. FIG. 1D shows a positive photoresist layer 12 deposited over the at least one metal layer 11 on the first wafer 10, and FIG. 2D shows a positive photoresist layer 22 deposited over the at least one metal layer 21 on the second wafer 20.

After application of the positive photoresist layer, UV light is impinged on portions of the positive photoresist layer of each of the first wafer and the second wafer to pattern the positive photoresist layer and expose regions of metal layer(s) on each of the first wafer and the second wafer. FIG. 1E shows the positive photoresist layer 12 following patterning thereof to define recesses 14 exposing portions of the at least one metal layer 11 over the first wafer 10, and FIG. 2E shows the positive photoresist layer 22 following patterning thereof to define recesses 24 exposing portions of the at least one metal layer 21 over the second wafer 20.

After patterning of the positive photoresist layer, exposed regions of the metal layer(s) each of the first wafer and the second wafer are wet etched to pattern the at least one metal layer. In a preferred embodiment where a gold layer is provided over a chromium adhesion layer, the gold layer may be wet etched using an etchant such as a type TFA ($KI-I_2$ complex) etchant or piranha solution (a mixture of sulfuric acid and hydrogen peroxide), and the chromium layer may be wet etched using a suitable chromium etchant, such as may involve perchloric, nitric, or acetic acid-based solutions. Various chromium etchants are commercially available from Cyantek, Inc. (Fremont, Calif., USA), including CR-3S, CR-5S, CR-7S, and CR-9S perchloric acid-based solutions; CR-4S nitric acid-based solution; and CR-14S acetic acid-based solution. FIG. 1F shows the first wafer 10, at least one metal layer 11, and positive photoresist layer 12 following wet etching of exposed portions of the at least one metal layer 11 to form recesses 15 therein. Similarly, FIG. 2F shows the second wafer 20, at least one metal layer 21, and positive photoresist layer 22 following wet etching of exposed portions of the at least one metal layer 21 to form recesses 25 therein.

Following wet etching of the at least one metal layer, the positive photoresist layer of each of the first wafer and the second wafer is removed, such as by using a microstripper cleaning chemical. FIG. 1G shows the first wafer 10 and patterned at least one metal layer 11 defining recesses 15, and FIG. 2G similarly shows the second wafer 20 and patterned at least one metal layer 21 defining recesses 25 therein.

Thereafter, one or more apertures are defined (e.g., using laser milling or another suitable hole-forming process) through the first wafer to serve as fluid access ports. After the one or more apertures are defined, the structure including the first wafer embodies a microfluidic device cover portion. FIG. 1H shows the first wafer 10 and patterned at least one metal layer 11, with formation of apertures (holes) 16 through the first wafer 10. The resulting structure including the first wafer 10 embodies a microfluidic device cover portion 18.

Turning to the base portion of the microfluidic device, a further fabrication step involves coating the second wafer with first negative photoresist to cover the patterned at least one metal layer. In certain embodiments, the first negative photoresist may include KMPR® 1000 series photoresist applied by spin coating to a thickness of about 50 microns. In certain embodiments, the first negative photoresist may be applied to a thickness in a range of from about 25 microns to about 50 microns, or in a range of from about 35 microns to about 500 microns. FIG. 2H illustrates the second wafer 20 and patterned at least one metal layer 21 following coating with a first negative photoresist 23.

A further fabrication step involves impinging UV light on portions of the first negative photoresist coating the second wafer to pattern the first negative photoresist layer, thereby defining recesses in the first negative photoresist and exposing regions of the at least one metal layer on the second wafer, to form a microfluidic device base portion. FIG. 2I illustrates the second wafer 20, patterned at least one metal layer 21, and patterned first negative photoresist layer 23 in which recesses 27 are defined to expose regions of the at least one metal layer 21 including recesses 25 in the at least one metal layer, with the resulting structure forming a microfluidic device base portion 28.

After the cover portion and base portion of the microfluidic device have been formed, such portions may be joined to one another with a negative photoresist (or UV adhesive) diffusive layer bonding technique. In certain embodiments, a second negative photoresist material or UV adhesive may be used. In certain embodiments, a second negative photoresist differing from the above-mentioned first negative photoresist may be used. In certain embodiments, a suitable negative photoresist for the diffusive bonding layer may embody a SU-8 family or KMPR® 1000 series negative photoresist. In certain embodiments, a UV adhesive such as Norland optical adhesive (commercially available from Norland Products, Cranbury, N.J., USA) may be used. Such negative photoresist or UV adhesive may be applied to one or both of the cover portion and the base portion of the microfluidic device. FIG. 3A is a exploded view of a microfluidic device prior to assembly thereof, including the cover portion 18 aligned with the base portion 28, with a negative photoresist (diffusive bonding) material layer 29 arranged between the cover portion 18 and the base portion 28. FIG. 3B illustrates the assembled microfluidic device 30 including the cover portion 18, the base portion 28, and the negative photoresist layer 29 joining the cover portion and the base portion. The resulting microfluidic device 30 includes recesses 27 that are bounded from above by the cover 18, with apertures 16 forming ports arranged to permit fluidic access to the recesses 27, and with surfaces of the metal layers 11, 21 exposed to the interior of the recesses 27 to serve as electrodes to provide electrocage utility.

Further aspects of the disclosure relate to a method of adjusting the viscosity of a cell culture medium used in live cell computed tomography by adding a long-chain polysaccharide to the medium. In certain embodiments, the aqueous solution comprises cell culture medium (e.g., a medium suitable for supporting cell life).

In certain embodiments, where a cell culture medium is provided, a cell culture medium includes a mixture of defined nutrients dissolved in a buffered physiological saline solution. In certain embodiments, a cell culture media includes salts, amino acids, sugar, vitamins, and other organic nutrients. As will be recognized by one skilled in the art, the selection of a basal cell medium for cell culture applications is primarily dependent on the chemical definition of the basal medium, the type of cell to be grown, and the culture system being employed.

In certain embodiments, the long-chain polysaccharide comprises at least one of Ficoll® and dextran polysaccharides. Ficoll® and dextran polysaccharides embody long-chain polysaccharides. Ficoll® (a registered trademark of GE Healthcare Bio-Sciences AB of Uppsala, Sweden) is a neutral, highly branched, high-mass, hydrophilic polysaccharide with radii ranging from 2-7 nm and which dissolves readily in aqueous solutions. Ficoll® polysaccharides embody copolymers of sucrose with epichlorohydrin. Ficoll® polysaccharides may have molecular weights ranging from 70 kDa to 400 kDa. FIG. 4A is a chemical diagram depicting the structure of a Ficoll® polysaccharide. Dextran is a complex, branched glucan (polysaccharide made of many glucose molecules) composed of chains of varying lengths, such as from 3 to 2000 kDa. FIG. 4B is a chemical diagram depicting the structure of a dextran polysaccharide.

In certain embodiments, the long-chain polysaccharide comprises molecular weight in a range of from about 10,000 to about 100,000 Da. In certain embodiments, the long-chain polysaccharide comprises molecular weight in a range of from about 100,000 to about 1,000,000 Da. In certain embodiments, the long-chain polysaccharide comprises molecular weight in a range of from about 1,000,000 to about 4,000,000 Da. In certain embodiments, the long-chain polysaccharide comprises molecular weight in a range of from about 100,000 to about 4,000,000 Da.

In certain embodiments, the concentration of said long-chain polysaccharide in said aqueous solution is in a range of from about 0.01% to about 0.1%. In certain embodiments, the concentration of said long-chain polysaccharide in said aqueous solution is in a range of from about 0.1% to about 1.0%. In certain embodiments, the concentration of said long-chain polysaccharide in said aqueous solution is in a range of from about 1.0% to about 10.0%. In certain embodiments, the concentration of said long-chain polysaccharide in said aqueous solution is in a range of from about 0.1% to about 10.0%. In certain embodiments, the preceding percentages embody weight percentages.

In certain embodiments, a method as disclosed herein further includes wetting at least one live cell or cell cluster with the aqueous solution, and/or introducing the aqueous solution and at least one live cell or cell cluster into a live cell computed tomography apparatus (optionally including a microfluidic device as disclosed herein).

In certain embodiments, a composition useful in live cell computer topography includes a long-chain polysaccharide at a concentration of from about 0.01% to about 10.0% in cell culture medium. In certain embodiments, the long-chain polysaccharide is selected from the group consisting of Ficoll® and Dextran polysaccharides.

Aspects and applications of the invention presented herein are described below in the drawings and detailed description of the invention. Unless specifically noted, it is intended that the words and phrases in the specification and the claims be given their plain, ordinary, and accustomed meaning to those of ordinary skill in the applicable arts. The inventor is fully aware that he can be his own lexicographer if desired. The inventor expressly elects, as his own lexicographer, to use only the plain and ordinary meaning of terms in the specification and claims unless he clearly states otherwise and then further, expressly sets forth the "special" definition of that term and explains how it differs from the plain and ordinary meaning. Absent such clear statements of intent to apply a "special" definition, it is the inventor's intent and desire that the simple, plain and ordinary meaning to the terms be applied to the interpretation of the specification and claims.

This disclosure has been prepared with awareness of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, this disclosure has been prepared with awareness of the standards and application of the special provisions of pre-AIA 35 U.S.C. § 112, ¶6 and post-AIA 35 U.S.C. § 112(f). Thus, any use of the words "function," "means" or "step" in the Detailed Description or Description of the Drawings or claims is not intended to somehow indicate a desire to invoke the special provisions of pre-AIA 35 U.S.C. § 112, ¶6 or post-AIA 35 U.S.C. § 112(f), to define the invention. To the contrary, if the provisions of pre-AIA 35 U.S.C. § 112, ¶6 or post-AIA 35 U.S.C. § 112(f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Invocation of the provisions of pre-AIA 35 U.S.C. § 112, ¶6 or post-AIA 35 U.S.C. § 112(f) is not intended, but even if such provisions are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

Those skilled in the art will recognize improvements and modifications to the preferred embodiments of the present disclosure. All such improvements and modifications are considered within the scope of the concepts disclosed herein and the claims that follow. Any of the various features and elements as disclosed herein may be combined with one or more other disclosed features and elements unless indicated to the contrary herein.

We claim:

1. A method of fabricating a microfluidic device useable to perform live cell computed tomography imaging, the method comprising:
   (a) cleaning a first wafer and a second wafer;
   (b) depositing at least one metal layer on each of the first wafer and the second wafer;
   (c) depositing a positive photoresist layer over the deposited at least one metal layer of each of the first wafer and the second wafer;
   (d) impinging UV light on portions of the positive photoresist layer of each of the first wafer and the second wafer to pattern the positive photoresist layer, and applying a first developer solution to wash away UV light-impinged portions of the positive photoresist layer, thereby defining recesses in the positive photoresist layer that expose regions of the at least one metal layer on each of the first wafer and the second wafer;
   (e) wet etching the exposed regions of the least one metal layer on each of the first wafer and the second wafer to pattern the at least one metal layer;
   (f) removing the positive photoresist layer of each of the first wafer and the second wafer;
   (g) defining at least one aperture through the first wafer, whereby after such at least one aperture is defined, a microfluidic device cover portion is obtained;
   (h) coating the second wafer with first negative photoresist to cover the patterned at least one metal layer;
   (i) impinging UV light on portions of the first negative photoresist coating the second wafer to pattern the first negative photoresist, and applying a second developer solution to wash away portions of the first negative photoresist not impinged by UV light, thereby producing recesses in the first negative photoresist that expose regions of the at least one metal layer on the second wafer, to form a microfluidic device base portion; and
   (j) applying a UV curable bonding agent to at least one of the microfluidic device cover portion or the microfluidic device base portion, arranging the microfluidic device cover portion and the microfluidic device base portion with the UV curable bonding agent in contact therebetween, and curing the UV curable bonding agent by impingement of UV light to accomplish joining between the microfluidic device cover portion and the microfluidic device base portion;
   wherein the resulting microfluidic device includes at least one cavity bounded by (i) patterned portions of the first negative photoresist, (ii) an exposed region of the at least one metal layer on the first wafer, and (iii) an exposed region of the at least one metal layer on the second wafer, and wherein the exposed region of the at least one metal layer on the first wafer and the exposed region of the at least one metal layer on the second wafer are configured as electrodes to provide electrocage utility.

2. The method of claim 1, wherein the at least one metal layer comprises a chromium layer and a gold layer.

3. The method of claim 2, wherein the chromium layer has a thickness in a range of from about 20 nm to about 40 nm.

4. The method of claim 2, wherein the gold layer has a thickness in a range of from about 100 nm to about 200 nm.

5. The method of claim 2, wherein said wet etching comprises etching the gold layer with an etchant selected from the group consisting of type TFA ($KI-I_2$ complex) and piranha solutions.

6. The method of claim 2, wherein said wet etching comprises etching the chromium layer with an etchant selected from the group consisting of perchloric acid-based, nitric acid-based, acetic acid-based, and piranha solutions.

7. The method of claim 1, wherein said positive photoresist layer comprises a mixture of propylene glycol monomethyl ether acetate (PGMEA) and ethyl lactate solvents.

8. The method of claim 1, wherein the positive photoresist layer has a thickness in a range of from about 1 µm to about 5 µm.

9. The method of claim 1, wherein said first negative photoresist comprises a KMPR® 1000 series or SU-8 family negative photoresist.

10. The method of claim 1, wherein the first negative photoresist has a thickness in a range of from about 25 µm to about 500 µm.

11. The method of claim 1, wherein said UV curable bonding agent comprises (i) a UV curable adhesive or (ii) a second negative photoresist including a SU-8 family or KMPR® 1000 series negative photoresist.

* * * * *